United States Patent
Bechert et al.

(10) Patent No.: US 7,605,298 B2
(45) Date of Patent: Oct. 20, 2009

(54) WOUND COVERING

(75) Inventors: Thorsten Bechert, Forchheim (DE); Peter Steinrucke, Erlangen (DE)

(73) Assignee: Bio-Gate AG, Nuremberg (DE)

( * ) Notice: Subject to any disclaimer, the term of this patent is extended or adjusted under 35 U.S.C. 154(b) by 0 days.

(21) Appl. No.: 10/585,606

(22) PCT Filed: Jan. 5, 2005

(86) PCT No.: PCT/EP2005/000048
§ 371 (c)(1),
(2), (4) Date: May 17, 2007

(87) PCT Pub. No.: WO2005/065603
PCT Pub. Date: Jul. 21, 2005

(65) Prior Publication Data
US 2007/0203442 A1 Aug. 30, 2007

(30) Foreign Application Priority Data
Jan. 9, 2004 (DE) .................. 10 2004 001 594

(51) Int. Cl.
*A61F 13/00* (2006.01)
(52) U.S. Cl. ............... 602/48; 602/42; 602/52; 602/54; 604/304
(58) Field of Classification Search ........... 602/41–59; 604/304–308; 424/443–449, 3
See application file for complete search history.

(56) References Cited

U.S. PATENT DOCUMENTS

| | | | |
|---|---|---|---|
| 4,728,323 A | 3/1988 | Matson | |
| 5,419,913 A | 5/1995 | Podell et al. | |
| 6,087,549 A * | 7/2000 | Flick | 602/41 |
| 6,333,093 B1 * | 12/2001 | Burrell et al. | 428/194 |
| 7,005,556 B1 * | 2/2006 | Becker et al. | 602/48 |
| 2002/0045049 A1 * | 4/2002 | Madsen | 428/423.3 |
| 2003/0176827 A1 * | 9/2003 | Chandra et al. | 602/48 |

FOREIGN PATENT DOCUMENTS

| | | |
|---|---|---|
| DE | 196 31 421 | 2/1998 |
| DE | 297 21 345 | 4/1998 |
| DE | 197 27 032 | 1/1999 |
| DE | 197 58 598 | 4/2000 |
| DE | 198 60 759 | 6/2000 |
| DE | 697 18 035 | 9/2003 |
| EP | 1 005 301 | 4/2003 |
| WO | WO 00/16913 | 3/2000 |
| WO | WO 00/16914 | 3/2000 |
| WO | WO 02/056927 | 7/2002 |
| WO | WO 2005/065603 | 7/2005 |

OTHER PUBLICATIONS

Bechert et al., "A new method for screening anti-infective biomaterials," *Nat. Med.*, 2000, 6(8):1053-1056.

* cited by examiner

*Primary Examiner*—Kim M Lewis
(74) *Attorney, Agent, or Firm*—Fish & Richardson P.C.

(57) ABSTRACT

The invention relates to a dressing for a wound, containing a first layer which is formed by an absorbent matrix and an antimicrobially active substance. The substance is provided on a surface of the matrix in a chemically or physically bonded matter. The surface of the matrix with the substance is coated with a hydrophilic polymer.

32 Claims, 2 Drawing Sheets

WOUND COVERING

CROSS-REFERENCE TO RELATED APPLICATIONS

Figure 1:
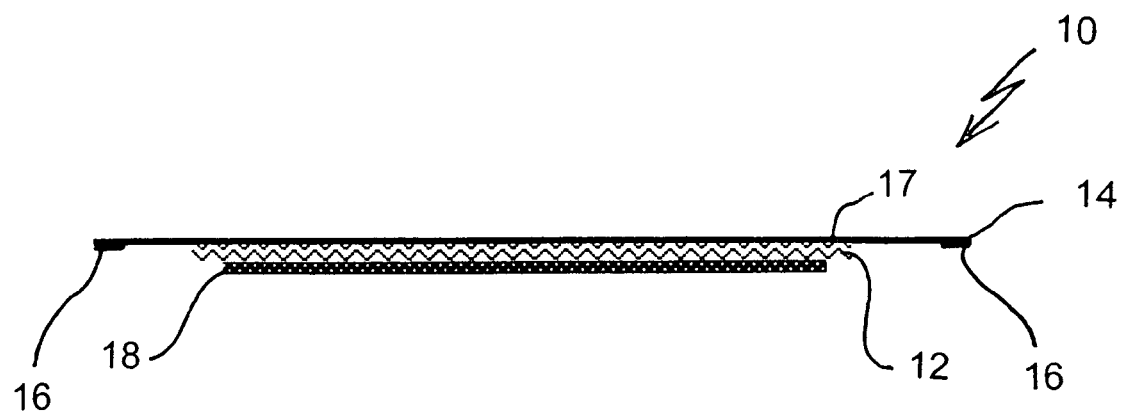

This application is a National Stage application under 35 U.S.C. §371 and claims benefit under 35 U.S.C. §119(a) of International Application No. PCT/EP2005/000048 having an International Filing Date of Jan. 5, 2005, which claims the benefit of priority of DE 102004 001 594.5 having a filing date of Jan. 9, 2004.

The invention relates to a wound covering.

It is generally known that the healing of wounds can be improved by a moist environment. Scab formation is prevented at the same time and scars seldom occur. The moist environment can be produced by media assisting wound healing. Customarily, for this purpose an absorbent material is impregnated with such a medium and then applied to a wound.

A wound plaster is known from DE 297 21 345 U1 in which a liquid chamber is provided between an adhesive film and a wound nonwoven. The liquid chamber can be placed such that liquid contained therein can thereby penetrate the wound nonwoven.

DE 196 31 421 A1 discloses an antimicrobial wound covering. The wound covering consists of a hydrophobic, bacteria-adsorbing material which contains an antimicrobial active compound which is not released into the wound. By means of the hydrophobic material in combination with the antimicrobial active compound, the bacteria from the wound fluid are adsorbed on the wound covering and destroyed there. By the removal of the wound covering, the bacteria are also removed. They thus no longer interfere with the course of healing.

A plaster is known from DE 197 27 032 A1 in which an adherent area is provided with a first adhesive zone and a second adhesive zone arranged outside the first adhesive zone. The adhesive power of the first adhesive zone is lower than that of the second adhesive zone.

A plaster is known from DE 198 60 759 C2 by means of which a skin surface can be covered into which an injection is to take place. The plaster consists of an elastic surface which has adhesive surfaces on the skin side, between which is arranged an annular medicinally active carrier of an absorbent material. The carrier contains a disinfectant for the disinfection of the injection zone enclosed by the carrier. The elastic surface is provided above the injection zone with an opening and a protective film which covers the adhesive surface and the medicinally active carrier and has to be removed before use.

An adhesive dressing having an adhesive composition in the form of a layer containing at least one section of an adjustable reinforcement is known from DE 697 18 035 T2. The adhesive composition and the reinforcement are selected such that the adhesive dressing is vapor-permeable.

A wound dressing for sticking onto the skin is known from EP 1 005 301 B1, a first area being provided which is opposite to a substrate which is provided for contact with a wound. The first area is surrounded by a second area which comprises an antimicrobial active compound in order to prevent migration of microorganisms into the first area from the external environment.

A multilayer dressing material is known from WO 02/056927 A2. It contains an absorbent layer, a gas-permeable but liquid-impermeable outer layer and a chamber in the absorbent layer for the release of a liquid treatment medium. The dressing material further contains a perforated layer forming a covering on the wound. The outer layer can be provided with an adhesive layer which makes possible fixing of the dressing material around the wound. By means of this dressing material, it is possible to keep a wound occlusive and moist.

It is the object of the present invention to make available a wound covering which makes possible even better wound healing. A process for its production should further be indicated.

According to the invention, a wound covering is provided comprising a first layer formed by an absorbent matrix and an antimicrobially active substance, the substance being present chemically or physically bonded to one surface of the matrix. The surface of the matrix including the substance is coated with a hydrophilic polymer. The matrix contains fibers and can consist of a nonwoven, of gauze, a foam material or another soft absorbent material. A foam material has the advantage that it can bind material discharging from the wound and thereby can be kept remote from the wound, so that it does not interfere with the healing process. The matrix can contain at least one fiber or be formed from at least one fiber. The surface of the matrix, to which the substance is bound, can then be a surface of the fiber. The substance is preferably bound to the fiber or surface of the matrix such that it cannot or can barely be floated away from the matrix in the case of use as intended.

A matrix or fiber in which the substance is present bound to the surface of the matrix or fiber can be produced, for example, by treating a polymer forming the matrix or fiber with the substance to produce the matrix or fiber. In the resulting matrix or fiber, some of the substance is present on the surface of the matrix or fiber. A larger part, however, is customarily embedded in the matrix or fiber by the polymer such that it is not accessible to liquid from outside.

Preferably, the substance is therefore exclusively bound to the surface of the matrix or fiber. As a result, in production an unnecessary amount of the substance must not be employed which is finally inaccessible.

A prerequisite for good wound healing is that in the matrix and a liquid surrounding the matrix no proliferation of undesired microorganisms occurs. In order to prevent this, the wound covering contains the antimicrobially active substance. A substance is antimicrobially active if it significantly delays or completely suppresses the proliferation of microorganisms, measured as described in DE 197 58 598 A1. An antimicrobially active substance is also a substance which, by conversion, produces an antimicrobial active compound in the environment in which the wound covering is to be used as intended. If, for example, the antimicrobial active compound is a metal ion or an ionic complex comprising the metal ion, the metal, its alloys and other substances from which the metal ion or the ionic complex comprising the metal ion can be released in the area of a wound are also antimicrobially active. The metal ion can be a silver, copper or zinc cation. The antimicrobially active substance can then be metallic silver, copper or zinc or an alloy or another substance from which the ion mentioned can be released in the area of a wound.

The antimicrobially active substance can be antimicrobially active against *Staphylococcus epidermidis* or other microorganisms. The antimicrobial activity of the substance with respect to other microorganisms is determined according to the process known from DE 197 58 598 A1 using the microorganism to be investigated in each case instead of *Staphylococcus epidermidis*. Particularly preferred substances are those which are antimicrobially active against one or more of the microorganisms from the group consisting of

*Bacillus, Clostridium, Enterobacter, Escherichia, Pseudomonas, Salmonella, Staphylococcus, Yersinia, Candida* and *Aspergillus*.

It has been found that an antimicrobially active substance, in particular if it is cytotoxic, can interfere with wound healing. The antimicrobially active substance is cytotoxic if it has a cytotoxic action as described in DIN-ISO 10993-5. In order to prevent interference, it is provided according to the invention that the substance is bonded to the surface of the matrix or the fibers of the matrix. By binding, it can be prevented that the antimicrobially active substance gets to an amount in the wound interfering with wound healing. Furthermore, it can be prevented thereby that the antimicrobially active substance is lost from the area of the wound covering by absorption into the body and as a result can no longer be antimicrobially active there long-term. Furthermore, it can be prevented thereby that the substance induces undesired, e.g. allergic, reactions in the body after absorption.

By means of the wound covering according to the invention, microorganisms originating from the wound, for example, can be prevented from proliferating in the wound and then leading to an infection or reinfection of the wound. By means of the long-term prevention of microorganism growth, the wound covering can be left on the wound until healing of the wound. As a result, mechanical stress on the wound by removal of the wound covering can be avoided and resting of the wound favorable to wound healing can be guaranteed. The main advantage of the wound covering according to the invention consists in the fact that the wound covering itself remains microorganism-free, while the wound healing process is not disturbed by the antimicrobially active substance.

The coating of the polymer is designed to be so thin and the polymer is chosen such that the action of the substance is not prevented thereby. Such a polymer can be, for example, a polymer formed from hexamethyl-disiloxane by plasma polymerization. The coating improves the binding of the substance to the fiber or the matrix. For example, clusters of silver applied by evaporation and deposition are protected from mechanical abrasion. Owing to the hydrophilicity of the layer, the wettability of the fiber or of the matrix is favored. A more uniform distribution of the liquid over the matrix is thereby achieved. Furthermore, a better action of the antimicrobially active substance can also be achieved by means of the improved contact of the fiber or of the matrix with the liquid. Moreover, by means of the hydrophilic polymer, in particular formed by plasma polymerization, an adhesion of gram-positive and/or gram-negative microorganisms to the fibers or the matrix can be decreased. Furthermore, the hydrophilic layer improves the gliding behavior of the matrix or individual fibers of the matrix in the moist environment, because a liquid film is formed directly on the surface of the coated matrix or fiber. If the matrix then lies on the wound, in the case of displacement it glides easily over the wound and in the course of this exerts only a low mechanical stress on the wound. As a result, in the case of a decreased liquid cushion between the matrix and the wound, the wearer comfort of the wound covering is markedly increased. Moreover, the liquid film on the coated fiber or matrix can also prevent the growth of the tissue newly formed in the wound into the matrix.

Preferably, the wound covering has a second layer formed by a gas-permeable but liquid-impermeable film connected to the matrix and a self-adhesive first area. The matrix is connected to the film in a second area. The matrix can be connected to the film, for example, in such a way that it is stuck together with or bonded to the film. The self-adhesive first area is an area of the film which surrounds the second area, preferably at a distance, it being possible to stick the wound covering to human or animal skin by means of the self-adhesive first area. As a result of sticking on, a liquid-tight inner space which can be filled with a liquid comprising the matrix is formed. The inner space makes possible liquid wound care.

This embodiment of the invention is based on the knowledge that during customary moist wound treatment the absorbent material begins to dry at an advanced phase of wound healing and the wound as a result extracts moisture. As a result, the course of wound healing is adversely affected.

Furthermore, this embodiment of the invention is based on the knowledge that wound healing can additionally be improved by the wound not only being kept moist, but being supplied with so much liquid that a liquid cushion is formed over the wound. As a result, wound healing is improved and the tendency for scar formation is reduced. Such wound care is designated here as liquid wound care. Using the wound covering according to the invention, this can be achieved by first placing the wound covering dry on the wound to be treated and firmly sticking it to the skin surrounding the wound by means of the self-adhesive first area such that the wound area is sealed liquid-tight as a result. Subsequently, the film can be pierced by means of a cannula and a liquid can be injected into the underlying inner space. After the withdrawal of the cannula, the resulting opening in the film can be sealed by means of an adhesive film. Advantageously, the liquid is administered a number of times, e.g. once per day. As a result, it can be ensured that the wound is permanently kept under a liquid cushion until healing and until the removal of the wound covering.

Preferably, the self-adhesive first area is provided with an adhesive which is highly skin-compatible and is not dissolved by an aqueous liquid. Such adhesives are known in the prior art, in particular in the field of plasters. Furthermore, the adhesive should also withstand an increased liquid pressure in the inner space without being detached from the skin. An increased liquid pressure can already be generated by the injection of the liquid and a tension exerted by the film. An increased liquid pressure can, for example, also be caused by a mechanical stress on the wound covering by the patient, e.g. by a movement of the body part containing the wound.

By virtue of the fact that the matrix is connected to the film, the matrix can be raised from the wound by means of the liquid cushion. As a result, the wound is not directly in contact with the matrix and the antimicrobially active substance. By raising the matrix from the wound, undesired growth of tissue newly formed in the wound into the matrix can also be avoided. A perforated layer forming a covering on the wound and separating the wound from the matrix, as is known from WO 02/056927 A2, is therefore not necessary. The matrix serves here as a carrier for the substance and not for the purpose of keeping the wound moist, as is the case with the known wound coverings. The raising of the matrix from the wound can be favored by the self-adhesive first area being arranged at a distance from a second area, to which the matrix is connected by the film.

Antisepsis of the wound can be achieved by means of an appropriate choice of the liquid. For example, the pH of the liquid can be so low that as a result growth of microorganisms is prevented. A liquid having a low pH moreover has an astringent action on the wound, whereby the healing process can be favored. Furthermore, the solution can contain factors and/or nutrients stimulating cell growth.

Preferably, the substance is an inorganic substance, in particular a metal or a metal compound. Such an antimicrobially active substance is usually inexpensive, easily obtainable and easy to process. A metal compound here is understood as meaning a mixture or an alloy of at least two metals. Metal ions or complexes comprising metal ions can be formed from the metal or the metal compound as active compounds and released. Preferably, an oligodynamically, i.e. in very small amounts, antimicrobially active metal or an oligodynamically antimicrobially active metal compound is concerned.

In a preferred embodiment, the substance is selected from a group consisting of silver, copper and zinc, their ions and their metal complexes or a mixture or alloy comprising at least one of these components. In addition to the metals mentioned, the alloy can in particular also contain gold and/or platinum. Such a substance acts against a large number of different microorganisms and intervenes in their metabolism in numerous ways. Accordingly, on use of such a substance resistance formation in bacteria occurs more rarely than when using specifically acting organic anti-microbial substances, such as antibiotics. Preferably, the substance is silver, a silver cation or a silver- or silver cation-releasing complex or a silver- or silver cation-releasing alloy. In particular, metallic silver is easily processable and obtainable in high quality at a comparatively low price, such that the wound covering according to the invention can also in turn be produced comparatively inexpensively.

The metal or the metal compound can be applied to the fiber or to the surface of the matrix in the form of clusters, in particular by evaporation and deposition, by a sputtering process or by chemical vapor deposition. In the case of evaporation and deposition, the metal or the metal compound is evaporated thermally in a vacuum and the metal vapor is subsequently deposited on the fiber or the matrix. The metal or the metal compound is present on the fiber or the matrix in the form of clusters as a result of application by means of evaporation and deposition, the sputtering process or chemical vapor deposition. The clusters have particularly good antimicrobial properties.

Expediently, the substance is present in the wound covering according to the invention in granular form, a mean grain or particle size of 5 to 100 nm being preferred. The substance can be present in the form of individual particles or particles interlinked with one another. Such fine powders of antimicrobially active substances can be easily produced, in particular for inorganic substances, and here in particular for silver, but also for copper and zinc, and also mixtures, complexes and alloys of the three metals mentioned. On account of the low mean grain size, the substance has a high specific surface area, so that it can be readily released from the matrix, in particular by diffusion. Furthermore, it is advantageous that, on account of the high specific surface area, chemical inactivation of the granular active compound, as can occasionally occur in a wound environments, usually only relates to a part of the surface, such that release of the substance from the matrix is made possible even under adverse conditions. A mean grain size of the substance of 5 to 50 nm, preferably 5 to 20 nm, has proven particularly advantageous. If the substance is silver or a silver alloy, these grain size distributions are also referred to as nanoscale silver or a nanoscale silver alloy.

The substance can be present in a layer thickness of at least 1 nm, and preferably not more than 1 mm. When using granular substances, the layer is at least as thick as the granular active compound. Preferably, the mean layer thickness is at least 5 nm to 100 nm, layer thicknesses of 10 nm to 50 nm being particularly preferred, in particular if the substance is silver, copper and/or zinc or their ions, metal complexes or a mixture or alloy of these elements. It has been shown that even such small layer thicknesses of an antimicrobial substance, in particular comprising nano-scale silver, are adequate in order to be able to achieve an antimicrobial but not cytotoxic action.

The substance is preferably present in an amount such that it acts antimicrobially in the case of thorough soaking of the matrix with a liquid in the matrix, in particular in the entire matrix. Such an amount can be determined by means of simple routine tests. If the substance is metallic silver, an adequate antimicrobial action in the matrix can be achieved by a silver content of the matrix of 1 µg to 200 µg per $cm^2$ of an area maximally coverable the matrix. Higher silver contents are disadvantageous, because silver ions can be released in such an amount that these have an adverse effect on wound healing.

Preferably, the polymer is a polymer decreasing the adhesion of bacteria, preferably gram-negative bacteria or staphylococci, in particular *Staphylococcus epidermidis*, to the fiber or matrix. In addition to the substance, this measure also causes a decreased colonization of the matrix with microorganisms.

Preferably, the fiber or surface of the matrix is coated with the polymer by means of plasma polymerization. As a result, an extremely thin embodiment of the layer is made possible, which barely adversely affects the action of the substance. By means of the choice of the parameters during the plasma polymerization, the properties of the polymer can be influenced. By carrying out customary routine tests, the person skilled in the art can determine suitable starting materials and parameters for the production of an appropriate polymer layer. The coating of the matrix with the antimicrobial substance and the plasma polymerization can be carried out, for example, as follows:

In a first step, clusters of nanoscale silver are applied to a matrix consisting of a nonwoven. For this purpose, metallic silver is evaporated at approximately 10 mbar working pressure under a protective gas atmosphere of, for example, argon. In this process, silver is deposited on the matrix in the form of individual silver particles or silver particles interlinked with one another. The mean particle size of the silver particles is approximately 10 to 20 nm. The silver is applied in a thickness of approximately 20 nm. In a second step, a plasma polymer layer containing hexamethyldisiloxane (HMDSO) is applied as a monomer or precursor. The plasma polymerization is carried out at a working pressure of 0.07 mbar using a working gas of 95% $O_2$ and 5% HMDSO. After 45 seconds of the plasma polymerization thus carried out, the silver applied is provided with a 45 nm thick and strongly hydrophilic plasma polymer layer. The surface energy of the coating here is 105 mN/m.

The application of the polymer to the fiber can take place before preparing the matrix from the fiber or afterward. If it takes place afterward, the entire matrix, for example a nonwoven or a textile fabric, is subjected to a coating process, such as plasma polymerization. It is particularly advantageous if the polymer is oxidized after the plasma polymerization. As a result, an extremely hydrophilic surface area can be created.

In a preferred embodiment, the polymer is formed from monomers based on acrylic acid or from monomers based on siloxane, in particular hexamethyldisiloxane. Such a polymer can combine antiadhesive properties to bacteria with good hydrophilic properties. It further allows a good action of a substance covered by the polymer on the matrix, such as, for example, metallic silver.

The polymer is preferably present in a layer having a mean thickness of 5 nm to 500 nm. In particular, in the case of a plasma-polymerized polymer, however, it is preferred if the thickness is 5 to 200 nm, preferably 10 to 100 nm. At these layer thicknesses, in particular with polymer layers produced by plasma polymerization, outstanding antimicrobial and noncytotoxic coatings can be produced. At the same time, these coatings are very thin, such that visually they are barely noticed or can even be transparent.

Preferably, the amount in which the substance is present is calculated such that the amount of active compounds formed and/or released by the substance does not act cytotoxically on a wound in the application case. Such an amount can be determined by means of simple routine tests. The active compounds can be, for example, metal ions or complexes of these metal ions. If the substance is silver, a suitable amount of silver in the matrix is, for example, 1 μg to 200 μg, preferably 5 μg to 35 μg, in particular 5 μg to 15 μg, per $cm^2$ of an area maximally coverable by the matrix. It has previously not been recognized that silver ions could be released by the silver-containing wound coverings customarily used in amounts which act cytotoxically on wounds. As a result, wound healing can be disturbed.

Preferably, substances assisting wound healing, in particular growth factors, are bound to the matrix. Such substances can be, for example, the epidermal growth factor (EGF), the platelet growth factor (PDGF), the vascular endothelial growth factor (VEGF) or the keratinocyte growth factor (KGF). Preferably, the matrix is thoroughly soaked or impregnated with a liquid assisting wound healing, in particular an acidic liquid or a liquid comprising nutrients assisting wound healing.

In a particularly preferred embodiment, the film is transparent, at least in places. As a result, the liquid level below the film can be observed and new liquid can be refilled as soon as a decreased liquid content is observed in the inner space.

In a further particularly advantageous embodiment of the invention, the entire wound covering, including matrix and film, is transparent to light, in particular UV light, infrared light (IR light) or near infrared light (NIR light).

This can be achieved by the choice of an appropriate material. As a result, it is possible to subject the wound to phototherapy without removing the wound covering. Phototherapy can considerably accelerate wound healing.

Preferably, the wound covering contains an indicator. The indicator can be a dye which indicates a certain state of the wound covering or the wound. For example, a pH indicator can be concerned here which can change its color depending on the pH. The color change can be observed through the film, which is transparent at least in places. The indicator can also be formed from a majority of substances which interact in order to indicate a certain condition. The indicator can also be a sensor. The sensor can be, for example, a conductive polymer which changes its conductivity according to the state of the wound or wound covering. The sensor can also be a biosensor. A biosensor is understood as meaning a measuring probe in which the biomolecules are coupled to transducers, such as, for example, potentiometric sensors. The transducers convert a signal resulting on binding of a specific substance to the biomolecule to an electrical signal. The sensor can be part of a sensor field or biosensor field comprising a number of sensors. By means of different sensors, a number of parameters characterizing the state of the wound or the wound covering can be determined simultaneously.

The indicator can also be an indicator which can indicate the liquid content of the matrix. As a result, drying of the matrix can be detected better and earlier. The indicator can also be an indicator which can indicate the degree and/or type of a microbial contamination of the matrix or of the wound. This can be achieved, for example, by means of an immuno-logical indicator. In this case, for example, microorganisms or parts of microorganisms can be specifically bound by an antibody and a color reaction induced as a result. The indicator can also be an indicator which can indicate an inflammatory status of the wound. Such an indicator can likewise be an immunological indicator. In this case, inflammatory factors can be specifically bound by an antibody and a color reaction induced as a result.

Furthermore, the invention relates to a process for the production of a wound covering according to the invention, having the following steps:
  making available of an absorbent matrix,
  making available of a gas-permeable but liquid-impermeable film,
  application of a self-adhesive first area (16) on or to the film and
  connection of the absorbent matrix to the film in a second area of the film, the first area surrounding the second area of the film, by means of evaporation and deposition, a sputtering process or chemical vapor deposition first an anti-microbially active substance and then, by plasma polymerization, a polymer being deposited on the matrix or a fiber forming the matrix.

The matrix can be a nonwoven, a gauze, a foam material or another soft absorbent material. The substance and the polymer can be deposited on the finished matrix. The fiber forming the matrix must not be a fiber which forms the matrix exclusively. The fiber forming the matrix can be a fiber which is incorporated into the matrix during or after the production of the matrix. By means of the evaporation and deposition, the sputtering process or chemical vapor deposition in combination with plasma polymerization, it is possible to achieve a particularly thin and simultaneously antimicrobially highly active application of the substance and a particularly thin application of the polymer having specific properties to the fiber or matrix. Only a small quantity of substance and/or polymer is needed. The substance is protected by the polymer, in particular from mechanical abrasion.

Figure 2:
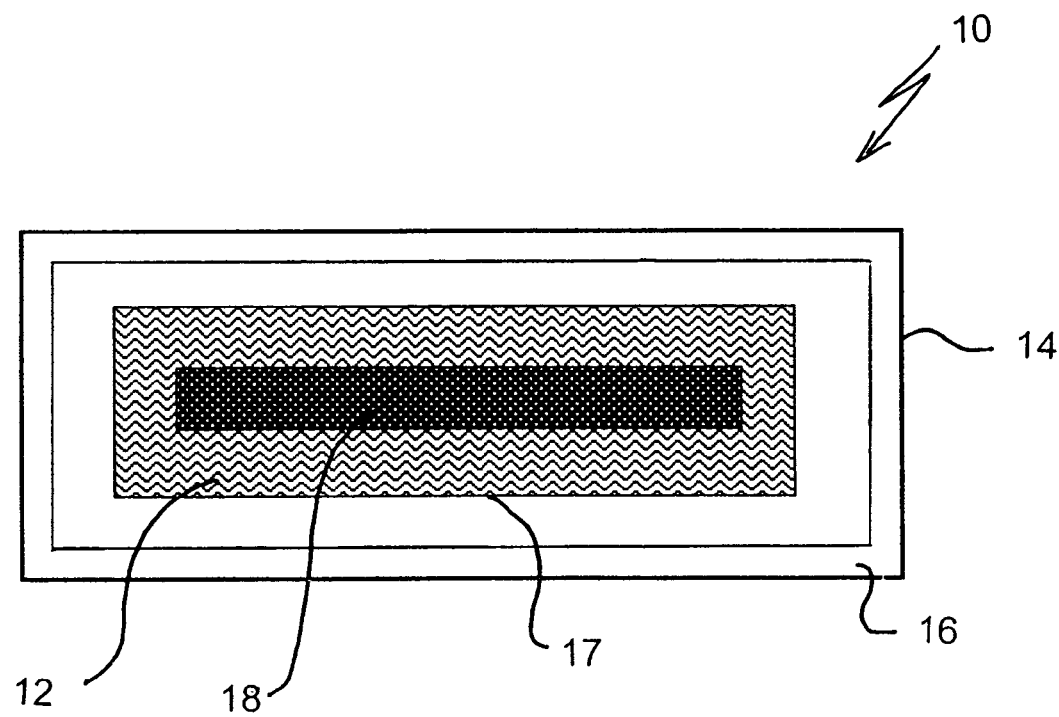
Figure 3:
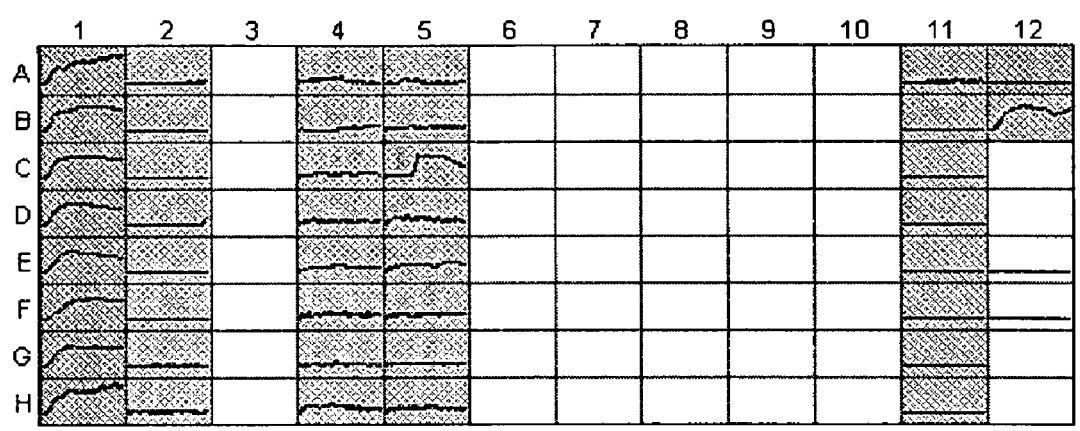

One embodiment of the invention is explained in more detail below by way of the drawings, in which:

FIG. 1 shows a schematic representation of the wound covering according to the invention in a side view, FIG. 2 shows a schematic representation of the wound covering according to the invention in a top view and FIG. 3 shows an arrangement of graphic representations of the time course of the growth of bacteria, measured in the form of optical density (OD) of a medium, in contact with a conventional matrix and a matrix of a wound covering according to the invention.

FIGS. 1 and 2 show a wound covering 10 according to the invention having an absorbent matrix 12, a gas-permeable but liquid-impermeable film 14 and a self-adhesive first area 16. The first area 16 is here an area of the film to which an adhesive is applied. The first area 16 here surrounds a second area 17 of the film contacting the matrix. On use of the wound covering 10 as intended, the matrix 12 is placed on the wound 18 and the self-adhesive first area 16 is stuck all around together with the skin surrounding the wound 18. Subsequently, a liquid can be injected through the film 14 into the inner space formed by sticking together. The hole formed on injecting into the film 14 is sealed by means of an adhesive film.

In an application study, in a first patient group a wound covering according to the invention having a matrix was employed whose fibers had been coated with silver and a hydrophilic polymer formed by plasma polymerization from hexamethyldisiloxane. The wound covering was in this case employed over at least 4 days for postoperative liquid wound care in the clinical picture of Pectus excavatum (funnel chest). In a second patient group serving as a control, conventional wound care was carried out. While in the second group infections occasionally occurred, in the first group no infections were observed. Moreover, the wearer comfort of the wound covering according to the invention was distinctly better than in the case of the wound covering employed for conventional wound care due to the hydrophilic coating. The liquid wound care with the wound covering according to the invention made possible a more rapid healing with a lower tendency for scar formation. The matrices of the wound coverings employed for wound care were also still antibacterially active after 4 days on a wound, as has been shown in the experiment presented in FIG. 3.

The results shown in FIG. 3 have been determined according to the process known from DE 197 58 598 A1. This process is further described in Bechert, Thorsten et al., Nature Medicine (2000), Vol. 6, No. 8, pages 1053 to 1056. The disclosure content of the two aforementioned documents is included here. The matrices to be tested were employed as described in the test.

In FIG. 3, each field shows an x-y graph, in which the time is plotted on the x-axis and the optical density is plotted on the y-axis. The experimental results shown in columns 1, 2, 4, 5, 11 and 12 of FIG. 3 have been determined in parallel experimental batches A to H corresponding to rows A to H using the following matrices:

Column 1, rows A-H: matrix uncoated,
Column 2, rows A-H: matrix coated with silver and a polymer formed from hexa-methyldisiloxane by plasma polymerization,
Column 4, rows A-H: matrix coated with silver and a polymer formed from hexa-methyldisiloxane by plasma polymerization from a first wound covering used for 4 days in the above application study,
Column 5, rows A-H: matrix coated with silver and a polymer formed from hexa-methyldisiloxane by plasma polymerization from a second wound covering used in the above application study for 4 days,
Column 11, rows A-H: sterile controls
Column 12, row A: positive control
Column 12, row B: negative control
Column 12, row E, F: blank value In the case of the sterile controls, in each case only medium without addition of *Staphylococcus epidermidis* was employed in order to show that the bacterial growth did not result from the medium. In the case of the positive control, a metallic silver-containing polymer was employed. The values show that the bacteria employed are sensitive to silver and can be destroyed by it. In the case of the negative control, the same polymer was employed that, however, contained no silver. The blank value is a value measured in an empty hollow of the microtiter plate, which is to be subtracted in an evaluation of all measurements.

The experimental results show that the matrix of the wound covering according to the invention coated with silver and the polymer formed from hexamethyl-disiloxane by plasma polymerization has a highly antibacterial or bactericidal action. This action is also still present after 4 days on a wound.

The invention claimed is:

1. A wound covering, wherein said wound covering comprises a first layer and a second layer,
    wherein said first layer comprises an absorbent matrix having a surface and an anti-microbially active substance, wherein said anti-microbially active substance is chemically or physically bonded to said surface, wherein the anti-microbially active substance is a metal, wherein said metal is in the form of clusters, wherein said surface and said substance are coated with a hydrophilic polymer, wherein said anti-microbially active substance is present in a layer having a mean thickness of 5 to 100 nm,
    wherein said second layer comprises a gas-permeable, liquid-impermeable film and a self-adhesive first area, wherein said second layer further comprises a second area, wherein said first area surrounds said second area, wherein said matrix is connected to said film in said second area, wherein said wound covering adheres to human or animal skin by means of said self-adhesive first area, wherein the adherence forms a liquid-tight inner space into which a liquid can be deposited.

2. The wound covering as claimed in claim 1, wherein said matrix has at least one fiber or is formed from at least one fiber and wherein the anti-microbially active substance is bound to a surface of said fiber.

3. The wound covering as claimed in claim 2, wherein said anti-microbially active substance is bound exclusively to the surface of said matrix or said fiber.

4. The wound covering as claimed in claim 1, wherein the anti-microbially active substance is selected from the group consisting of silver, copper, zinc, a mixture of silver, copper and zinc, and a mixture or alloy comprising at least one of these components.

5. The wound covering as claimed in claim 1, wherein said clusters of said metal is applied to said matrix surface by evaporation and deposition, by a sputtering process, or by chemical vapor deposition.

6. The wound covering as claimed in claim 1, wherein the anti-microbially active substance has a mean particle size of 5 to 100 nm.

7. The wound covering as claimed in claim 1, wherein the anti-microbially active substance is present in an amount which is anti-microbially active upon thorough soaking of the matrix with a liquid in the matrix.

8. The wound covering as claimed in claim 1, wherein the hydrophilic polymer is a polymer that decreases the adhesion of bacteria to said matrix.

9. The wound covering as claimed in claim 8, wherein the bacteria is a gram-negative bacteria.

10. The wound covering as claimed in claim 9, wherein the bacteria is *Staphylococcus epidermidis*.

11. The wound covering as claimed in claim 1, wherein said surface of said matrix is coated with said hydrophilic polymer by means of plasma polymerization.

12. The wound covering as claimed in claim 1, wherein the hydrophilic polymer is oxidized.

13. The wound covering as claimed in claim 1, wherein said hydrophilic polymer is formed from monomers based on acrylic acid or from monomers based on siloxane.

14. The wound covering as claimed in claim 13, wherein said siloxane is hexamethyldisiloxane.

15. The wound covering as claimed in claim 1, wherein the hydrophilic polymer is present in a layer having a mean thickness of 5 to 500 nm.

16. The wound covering as claimed in claim 1, wherein the anti-microbially active substance is present in an amount in which an amount of active compounds not acting cytotoxically on a wound is formed and/or released by said substance.

17. The wound covering as claimed in claim 1, wherein said matrix further comprises one or more substances that assist wound healing.

18. The wound covering as claimed in claim 17, wherein said one or more substances that assist wound healing are growth factors.

19. The wound covering as claimed in claim 1, wherein said matrix is thoroughly soaked or impregnated with a liquid that assists in wound healing.

20. The wound covering as claimed in claim 19, wherein said liquid is an acidic liquid or a liquid comprising nutrients.

21. The wound covering as claimed in claim 1, wherein said film is transparent.

22. The wound covering as claimed in claim 1, wherein said wound covering is transparent to light.

23. The wound covering as claimed in claim 22, wherein said light is UV light, JR light, or NIR light.

24. The wound covering as claimed in claim 1, wherein said wound covering further comprises an indicator.

25. The wound covering as claimed in claim 24, wherein said indicator is a pH indicator.

26. The wound covering as claimed in claim 24, wherein the indicator is a sensor.

27. The wound covering as claimed in claim 26, wherein said sensor is a biosensor.

28. The wound covering as claimed in claim 26, wherein the sensor is a conductive polymer which changes its conductivity depending on the state of the wound or wound covering.

29. The wound covering as claimed in claim 24, wherein said indicator indicates the liquid content of said matrix.

30. The wound covering as claimed in claim 24, wherein the indicator indicates the degree and/or type of a microbial contamination of said matrix or of a wound.

31. The wound covering as claimed in claim 24, wherein the indicator indicates an inflammatory status of a wound.

32. A process for the production of the wound covering as claimed in claim 1, comprising the following steps:
   providing an absorbent matrix,
   providing a gas-permeable but liquid-impermeable film,
   applying a self-adhesive first area on or to said film,
   connecting said absorbent matrix to said film in a second area of said film, wherein the first area surrounds the second area,
   depositing an anti-microbially active substance onto said matrix, wherein said depositing is by evaporation and deposition, by a sputtering process or by chemical vapor deposition, and
   depositing a hydrophilic polymer onto said matrix, wherein said depositing is by plasma polymerization.

* * * * *